(12) United States Patent
Rasch

(10) Patent No.: US 12,127,869 B2
(45) Date of Patent: Oct. 29, 2024

(54) PROTECTIVE CASE FOR HANDHELD X-RAY EMITTER DEVICE AND X-RAY EMITTER DEVICE WITH PROTECTIVE CASE

(71) Applicant: Michael G. Rasch, Holladay, UT (US)

(72) Inventor: Michael G. Rasch, Holladay, UT (US)

(73) Assignee: Michael G. Rasch, Holladay, UT (US)

( * ) Notice: Subject to any disclaimer, the term of this patent is extended or adjusted under 35 U.S.C. 154(b) by 393 days.

(21) Appl. No.: 17/737,467

(22) Filed: May 5, 2022

(65) Prior Publication Data

US 2023/0355193 A1 Nov. 9, 2023

(51) Int. Cl.
*A61B 6/00* (2024.01)
*H05G 1/04* (2006.01)

(52) U.S. Cl.
CPC .............. *A61B 6/4405* (2013.01); *H05G 1/04* (2013.01)

(58) Field of Classification Search
CPC ... H05G 1/04; H05G 1/26; A61B 6/40; A61B 6/51; A61B 6/4405; A61B 6/08; A61B 6/107; A61B 6/00; A61B 6/10; A61B 6/14; A61B 6/4035; A61B 6/405; A61B 1/00105; A61B 8/0833; A61B 8/12; A61B 1/31; A61B 2017/00734; A61B 8/4455; A61B 5/0059; A61B 6/145; A61B 5/061; A61B 6/4233; A61B 6/512; A61B 6/547; A61B 6/4441; A61B 6/467; G01N 23/223; G01N 2223/076; G01N 23/043; G21K 4/00
USPC .......................... 378/197, 102, 103, 201, 203
See application file for complete search history.

(56) References Cited

U.S. PATENT DOCUMENTS

| | | | | |
|---|---|---|---|---|
| 4,979,198 A | * | 12/1990 | Malcolm ................... | H05G 1/26 378/102 |
| 5,077,771 A | * | 12/1991 | Skillicorn ................ | H05G 1/06 378/102 |
| 5,631,943 A | * | 5/1997 | Miles ....................... | A61B 6/548 378/102 |
| 7,448,802 B2 | * | 11/2008 | Oettinger .................. | H05G 1/06 378/102 |
| 2006/0098779 A1 | * | 5/2006 | Turner ..................... | A61B 6/505 378/102 |

* cited by examiner

*Primary Examiner* — Irakli Kiknadze
(74) *Attorney, Agent, or Firm* — WORKMAN NYDEGGER

(57) ABSTRACT

A protective case for a handheld x-ray emitter device, and a handheld x-ray emitter device protected by the protective case. Conventional handheld x-ray emitter devices include a tube barrel and a trigger handle connected to the tube barrel. The junction where the trigger handle connects to the tube barrel can be a point of structural weakness in the handheld x-ray emitter device. The protective case covers portions of the handheld x-ray emitter device so as to structurally reinforce the junction between the tube barrel and trigger handle, while still allowing the handheld x-ray emitter device to be operated.

20 Claims, 9 Drawing Sheets

PROTECTIVE CASE FOR HANDHELD X-RAY EMITTER DEVICE AND X-RAY EMITTER DEVICE WITH PROTECTIVE CASE

BACKGROUND

An x-ray emitter device emits a penetrating form of high-energy electromagnetic radiation (called "x-rays" or "x-ray beams") through the body of a medical patient. X-rays more easily pass through soft tissue (such as skin, muscles, fat and organs), but are absorbed by harder materials (such as bones and teeth) of the medical patient. Accordingly, an x-ray detector device can be positioned to receive the x-rays emitted by the x-ray emitter device, and image internal structures of the patient. Areas of higher absorption correspond to bone and teeth structures and generally appear white in an x-ray image. Furthermore, in such a typical system, softer tissue appears in shades of gray, and air appears black. X-ray technology is used in a wide variety of medical and dental professions.

A handheld version of such an x-ray emitter device is often used in the field of dentistry. In such a system, the handheld x-ray emitter device is held in the hand of a dentist or dental assistant, directed towards an appropriate area of the mouth of a patient, and then activated. Responsively, the handheld x-ray emitter device emits low intensity x-ray beams into the mouth of the patient. The electromagnetic radiation passes through the soft tissue in the mouth region, whereas the teeth and jawbone of the patient absorbs the electromagnetic radiation. The x-ray detector device is then used to produce an x-ray image that allows the dental professional to evaluate the structural features of the teeth and jawbone of the patient. Specifically, these images help dental professionals to locate cavities, observe the overall health of the tooth and bone surrounding the tooth, and observe the status of developing teeth in children.

The subject matter claimed herein is not limited to embodiments that solve any disadvantages or that operate only in environments such as those described above. Rather, this background is only provided to illustrate one exemplary technology area where some embodiments describe herein may be practiced.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments described herein relate to a protective case for a handheld x-ray emitter device, and to a handheld x-ray emitter device protected by the protective case. As an example, the protected handheld x-ray emitter device could be a handheld x-ray emitter device used in dentistry, such as the NOMAD™ Pro 2 handheld x-ray system. Conventional handheld x-ray emitter devices include a tube barrel and a trigger handle connected to the tube barrel. The tube barrel is quite heavy as it includes the equipment used to generate high frequency x-rays. The junction where the trigger handle connects to the tube barrel can be a point of structural weakness in the handheld x-ray emitter device. This weakness is caused by the significant weight of the tube barrel, and the small size of the junction where the trigger handle connects to the tube barrel.

In accordance with the principles described herein, a protective case is provided that prevents damage to the handheld x-ray emitter device. The protective case includes a left component and a right component. The left component covers at least a part of a left portion of the handheld x-ray emitter device including at least a part of a left portion of the tube barrel of the handheld x-ray emitter device. The right component covers at least a part of a right portion of the handheld x-ray emitter device including at least a part of a right portion of the tube barrel of the handheld x-ray emitter device.

When the right component and the left component are coupled to each other and contain the handheld x-ray emitter device, the coupled combination of the left component and the right component collectively includes a handle portion that covers a majority of the trigger handle of the handheld x-ray emitter device. However, in this case, a trigger of the trigger handle is still activatable. In this manner, the handheld x-ray emitter device is capable of being used, even while inside of the protective case.

Additionally, when the right component and left component are coupled together and contain the handheld x-ray emitter device, the coupled combination of the left component and right component includes a tube portion that encircles at least some of the tube barrel. Furthermore, the tube portion of the coupled combination is integrally connected to the handle portion of the coupled combination so that the protective case structurally reinforces a connection between the tube barrel and the trigger handle of the handheld x-ray emitter device. This structurally reinforces the junction where the trigger handle connects to the tube handle, even while the handheld x-ray emitter device is being used.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and details through the use of the accompanying drawings in which.

DETAILED DESCRIPTION

Embodiments described herein relate to a protective case for a handheld x-ray emitter device, and to a handheld x-ray emitter device protected by the protective case. As an example, the protected handheld x-ray emitter device could be a handheld x-ray emitter device used in dentistry, such as the NOMAD™ Pro 2 handheld x-ray system. Conventional handheld x-ray emitter devices include a tube barrel and a trigger handle connected to the tube barrel. The tube barrel is quite heavy as it includes the equipment used to generate high frequency x-rays. The junction where the trigger handle connects to the tube barrel can be a point of structural weakness in the handheld x-ray emitter device. This weakness is caused by the significant weight of the tube barrel, and the small size of the junction where the trigger handle connects to the tube barrel.

In accordance with the principles described herein, a protective case is provided that prevents damage to the handheld x-ray emitter device. The protective case includes a left component and a right component. The left component covers at least a part of a left portion of the handheld x-ray emitter device including at least a part of a left portion of the tube barrel of the handheld x-ray emitter device. The right component covers at least a part of a right portion of the handheld x-ray emitter device including at least a part of a right portion of the tube barrel of the handheld x-ray emitter device.

When the right component and the left component are coupled to each other and contain the handheld x-ray emitter device, the coupled combination of the left component and the right component collectively includes a handle portion that covers a majority of the trigger handle of the handheld x-ray emitter device. However, in this case, a trigger of the trigger handle is still activatable. In this manner, the handheld x-ray emitter device is capable of being used, even while inside of the protective case.

Additionally, when the right component and left component are coupled together and contain the handheld x-ray emitter device, the coupled combination of the left component and right component includes a tube portion that encircles at least some of the tube barrel. Furthermore, the tube portion of the coupled combination is integrally connected to the handle portion of the coupled combination so that the protective case structurally reinforces a connection between the tube barrel and the trigger handle of the handheld x-ray emitter device. This structurally reinforces the junction where the trigger handle connects to the tube handle, even while the handheld x-ray emitter device is being used.

Figure 1:
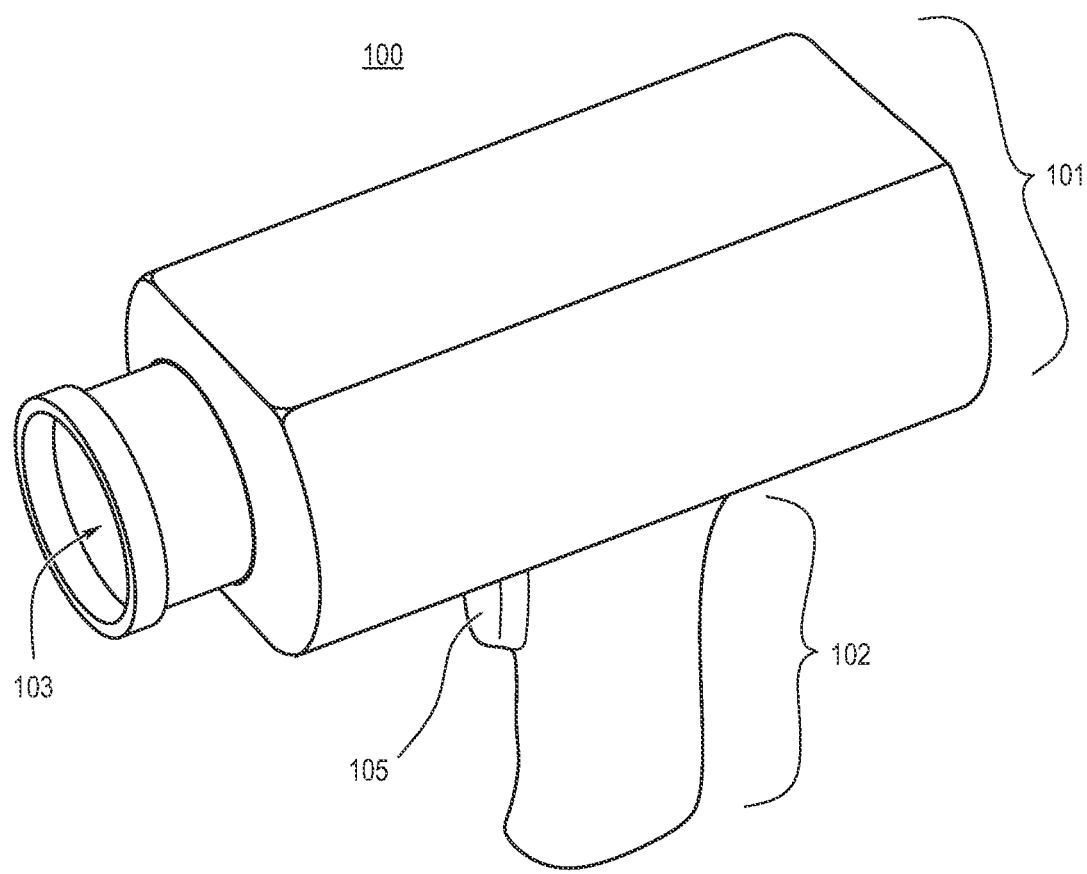
FIG. 1 illustrates a generic handheld x-ray emitter device.

FIG. 1 abstractly illustrates a handheld x-ray emitter device 100. The handheld x-ray emitter device 100 is shown in generic form for simplicity only, and to merely introduce different components of a typical handheld x-ray emitter device. A specific example of a handheld x-ray emitter device 100 will be illustrated with respect to FIGS. 2A and 2B. However, the handheld x-ray emitter device 100 is illustrated more generically in order to emphasize that the principles described herein are not limited to the protection of any particular handheld x-ray emitter device.

The handheld x-ray emitter device 100 is comprised of a tube barrel 101 and a trigger handle 102 connected to the tube barrel 101. The tube barrel 101 is heavy as it contains the mechanisms required to generate x-rays and propagate the x-rays along the length of the tube barrel 101 for emission out of the front portion 103 of the tube barrel 101. The trigger handle 102 includes a trigger 105 which, when activated, causes x-rays to be emitted out of the front portion 103 of the tube barrel 101.

Figure 2A:
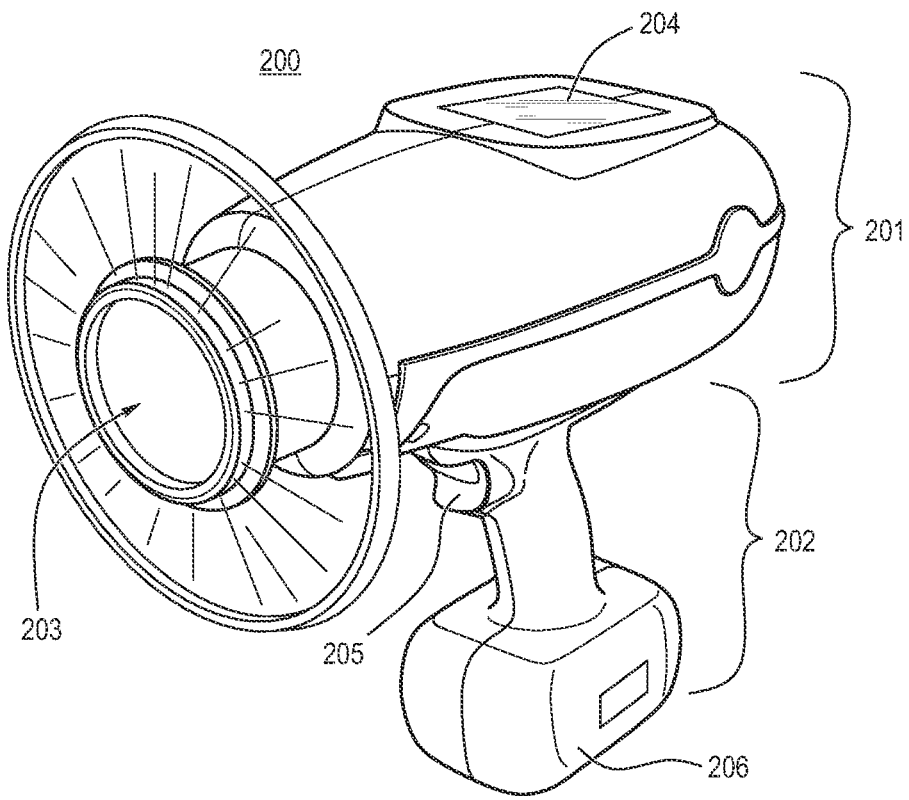
FIG. 2A illustrates a left perspective view of a handheld x-ray emitter device that is an example of the handheld x-ray emitter device of FIG. 1.
Figure 2B:
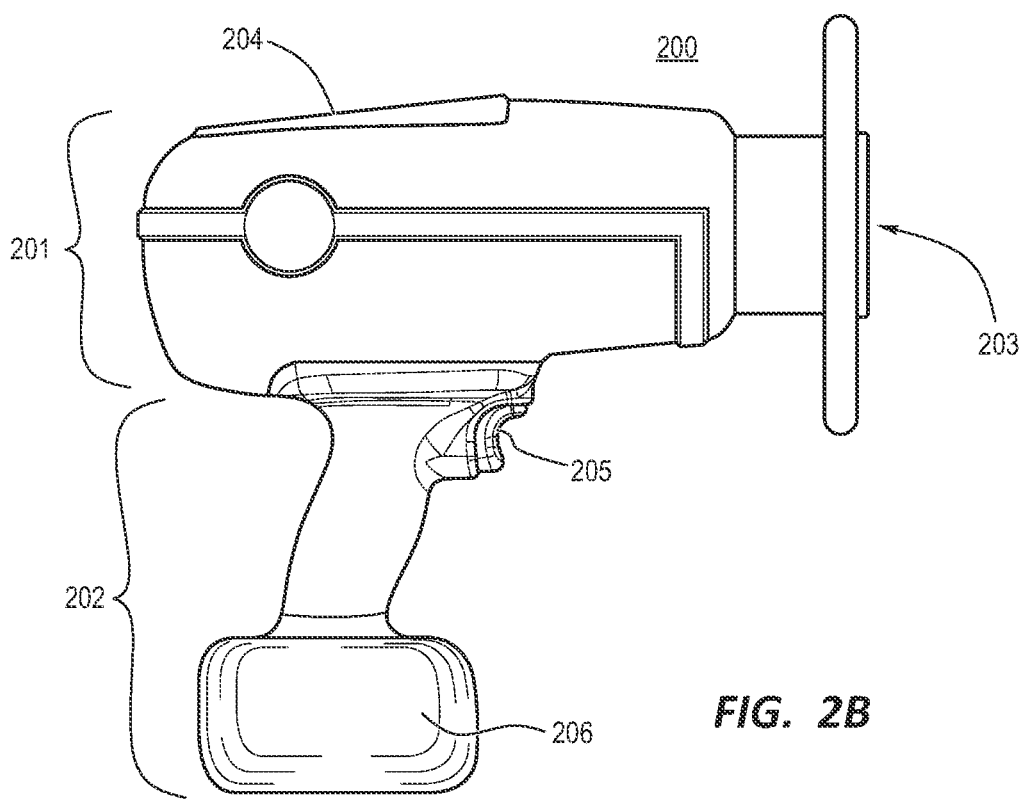
FIG. 2B illustrates a right side view of the handheld x-ray emitter device of FIG. 2A.

FIGS. 2A and 2B illustrate a handheld x-ray emitter device 200, which is an example of the handheld x-ray emitter device 100 illustrated in FIG. 1. FIG. 2A illustrates a left (from the left) perspective view of the handheld x-ray emitter device 200. FIG. 2B illustrates a right side view of the handheld x-ray emitter device 200. As an example, the handheld x-ray emitter device 200 may be the NOMAD™ Pro 2 handheld x-ray system.

The handheld x-ray emitter device 200 includes a tube barrel 201 and a trigger handle 202. The tube barrel 201 is an example of the tube barrel 101 of FIG. 1, and the trigger handle 202 is an example of the trigger handle 102 of FIG. 1. The tube barrel 201 includes a front portion 203, which is an example of the front portion 103 of FIG. 1. The tube barrel 201 also has a display 204 disposed on the top of the tube barrel 201 so that the display 204 can be viewed by the operator of the handheld x-ray emitter device 200. The trigger handle 202 includes a trigger 205, which is an example of the trigger 105 of FIG. 1. Activation of the trigger 205 allows for the emission of x-rays out of the front portion 203 of the tube barrel 201.

The handheld x-ray emitter device 200 includes a battery portion 206 that is connected to the trigger handle 202 at an end of the trigger handle 202 that is opposite the end of the trigger handle 202 to which the tube barrel 201 is connected. That is, while the tube barrel 201 is connected to the top of the trigger handle 202, the battery portion 206 is connected at the bottom of the trigger handle 202.

Figure 3:
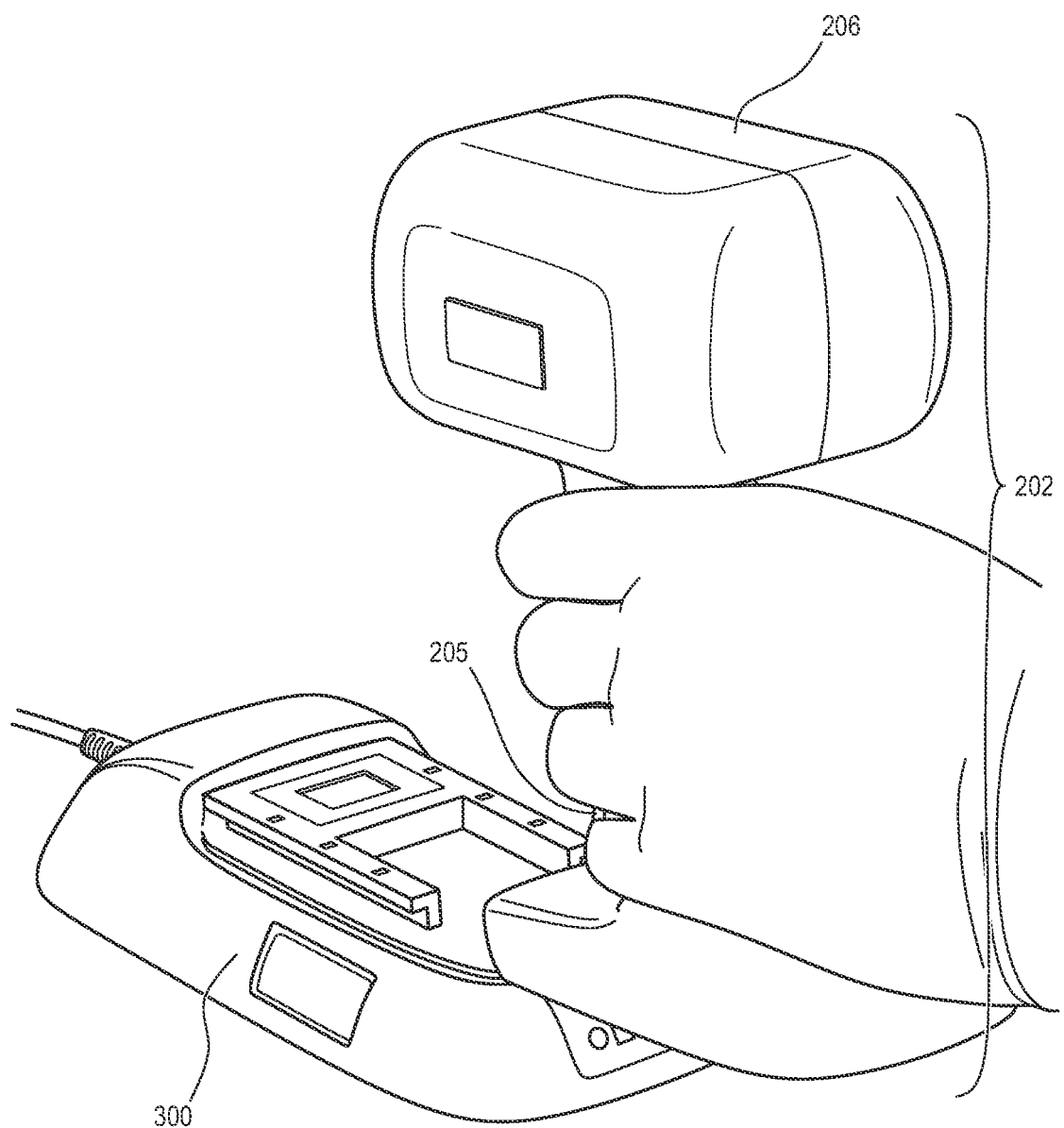
FIG. 3 illustrates a configuration of the handheld x-ray emitter device of FIGS. 2A and 2B, but in which the trigger handle has been removed from the tube barrel in preparation for charging.

FIG. 3 illustrates a configuration of the handheld x-ray emitter device of FIGS. 2A and 2B, but in which the trigger handle 202 has been removed from the tube barrel (not shown in FIG. 3). In this configuration, the trigger handle 202 is ready to slide into a charging cradle 300 to perform charging of the battery located within the battery portion 206 of the trigger handle 202. After charging has completed, the trigger handle 202 may be reconnected to the tube barrel 201 to resume usage of the handheld x-ray emitter device 200 now with the recharged battery. In accordance with some embodiments described herein, the trigger handle 202 can be slidably removed from the tube barrel 201 even when there is a protective case that is protecting the x-ray emitter device and that is structurally reinforcing the junction between the trigger handle 202 and the tube barrel 201.

The junction between the tube barrel 201 and the trigger handle 202 is a point of structural weakness. This is because the tube barrel 201 is heavy, including the mechanisms that generate x-rays. Accordingly, even when the trigger handle 202 is maneuvered in a normal way, the maneuvering can cause considerable stresses within or proximate this junction. Thus, over time, the junction can become structurally fatigued and even structurally fail. In accordance with the principles described herein, a protective case structurally reinforces this junction, resulting in extended life of the handheld x-ray emitter device. An example of such a protective case will now be described with respect to FIGS. 4A and 4B and subsequent figures.

Figure 4A:
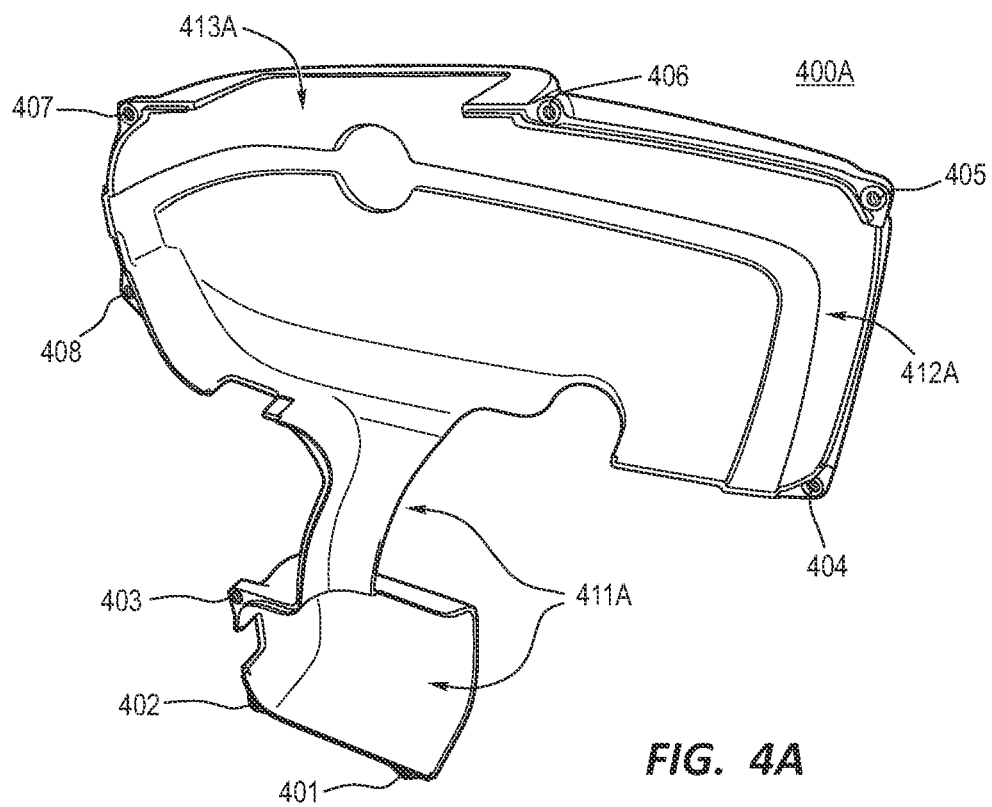
FIG. 4A illustrates a right perspective view of the inside of the left component of a protective case, which represents an example of a protective case in accordance with the principles described herein.
Figure 4B:
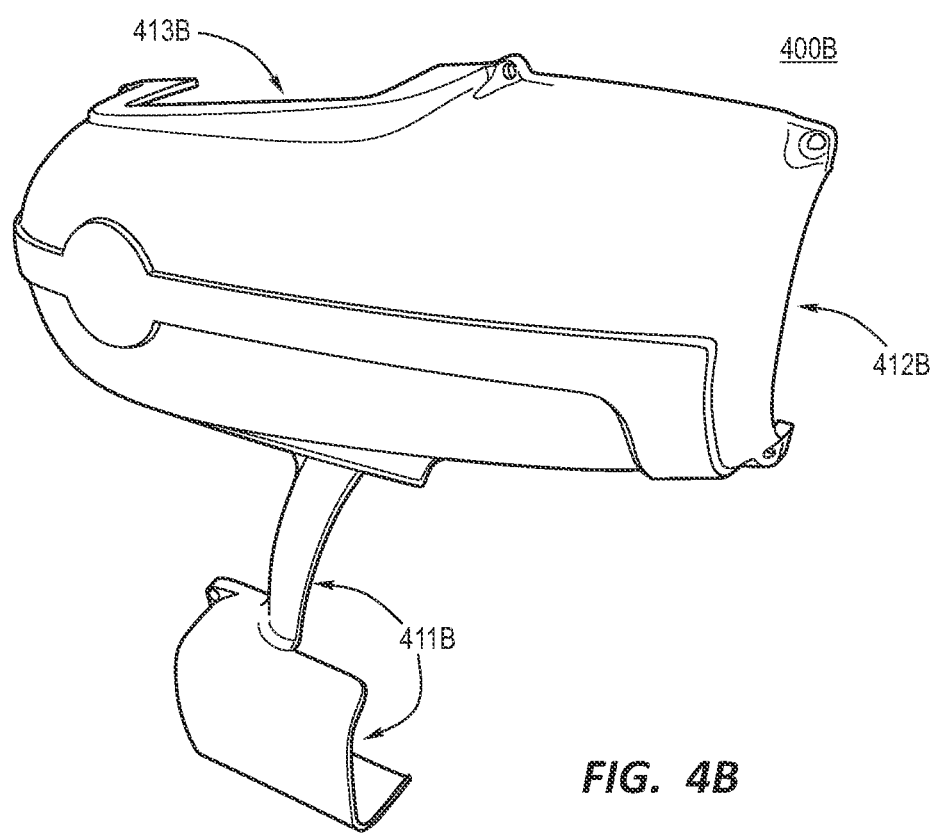
FIG. 4B illustrates a right perspective view of the outside of the right component of a protective case, which is configured to mate with the left component to thereby cover the handheld x-ray emitter device of FIG. 2.

FIGS. 4A and 4B illustrate an example of a protective case for the handheld x-ray emitter device 200. The protective case is comprised of a left component 400A and a right component 400B. FIG. 4A illustrates a right perspective view of the left component 400A showing the inside of the left component 400A. FIG. 4B illustrates a right perspective view of the right component 400B showing the outside of the right component 400B. In this example, the left component 400A and the right component 400B are essentially structurally mirrored.

The left component 400A is structured to cover a left portion of the handheld x-ray emitter device 200. The right component 400B is structured to cover a right portion of the handheld x-ray emitter device 200. The left component 400A and the right component 400B are configured to connect with each other to thereby serve as a protective case for the handheld x-ray emitter device 200, while still allowing the handheld x-ray emitter device 200 to functionally operate. That is, a hand may still wrap around the tube barrel 201 via the protective case, the trigger 205 is still activatable, the display 204 still visible and the x-ray emission being unimpeded.

While the protected handheld x-ray emitter device 200 may be slightly heavier than an unprotected handheld x-ray emitter device 200, the weight of the protective case is relatively insubstantial. In one embodiment, each of the left component 400A and right component 400B are composed of a non-gelatinous solid material, such as plastic. The material should be a non-gelatinous solid material so as to structurally reinforce the junction between the trigger handle 202 and the tube barrel 201. The material should also be preferably light weight and strong, such as plastic.

The left component 400A and right component 400B are removably couplable to each other. For example, the left component 400A and right component 400B can be coupled together via one or more screws attached through one or more screw holes. For instance, as best seen in FIG. 4A, there are eight screw holes 401 through 408 formed in the left component 400A. There are also corresponding screw holes formed in the right component 400B, some of which being visible in FIG. 4B. one or more latches 401 formed in the combination of the left component 400A and right component 400B.

Figure 5A:
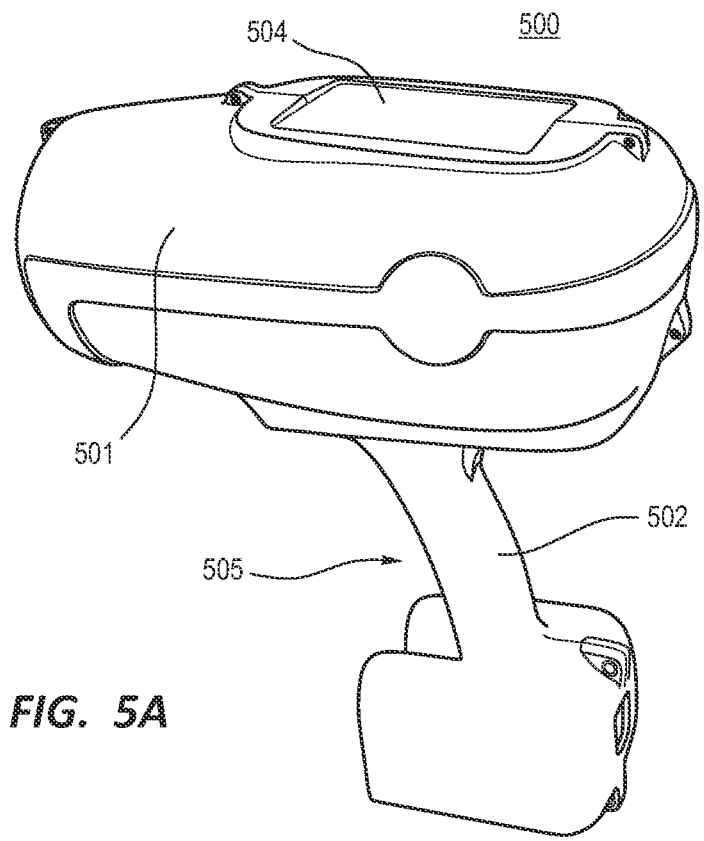
FIG. 5A is a left-back perspective view of the protective case composed by coupling the left component of FIG. 4A with the right component of FIG. 4B.
Figure 5B:
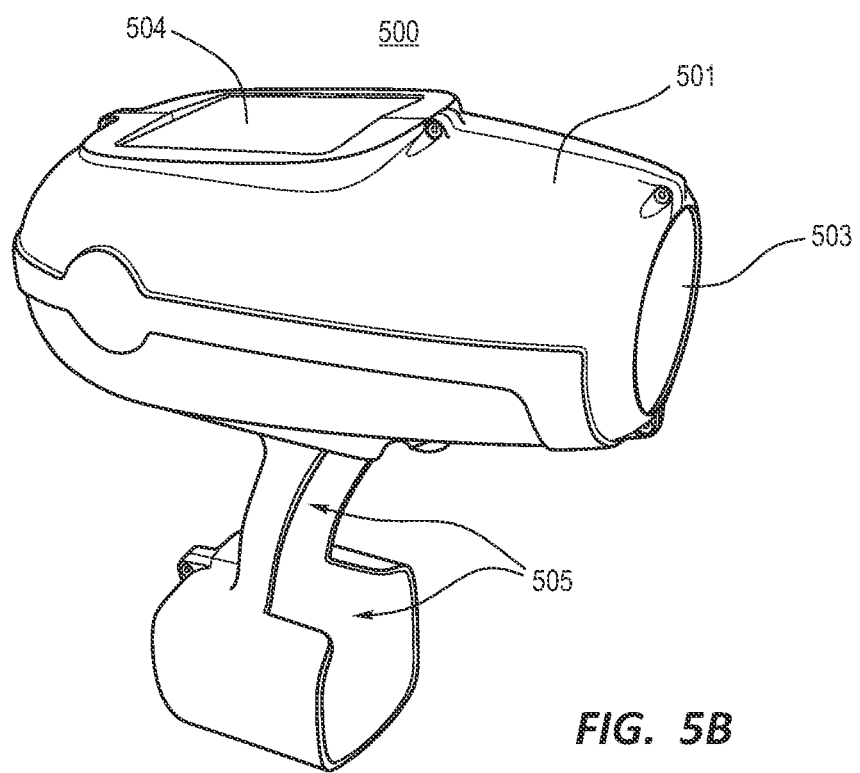
FIG. 5B is a right-front perspective view of the protective case of FIG. 5B.

FIGS. 5A and 5B illustrates the left component 400A and right component 400B coupled together (herein referred to as the "closed state"). Note that now the left component and the right component are now fastened by screws. The combination of the left component 400A and right component 400B in the closed state will be referred to hereinafter as the protective case 500. FIG. 5A is a left-back perspective view of the protective case 500. FIG. 5B is a right-front perspective view of the protective case.

In the description and in the claims, the collective combination of the left component 400A and the right component 400B in the closed state will be often referred to as "the coupled combination of the left component and the right component" or more simply "the coupled combination". Furthermore, unless otherwise referencing a specific component of the protective case 500, "the protective case" refers to the coupled combination of left and right components.

Figure 6A:
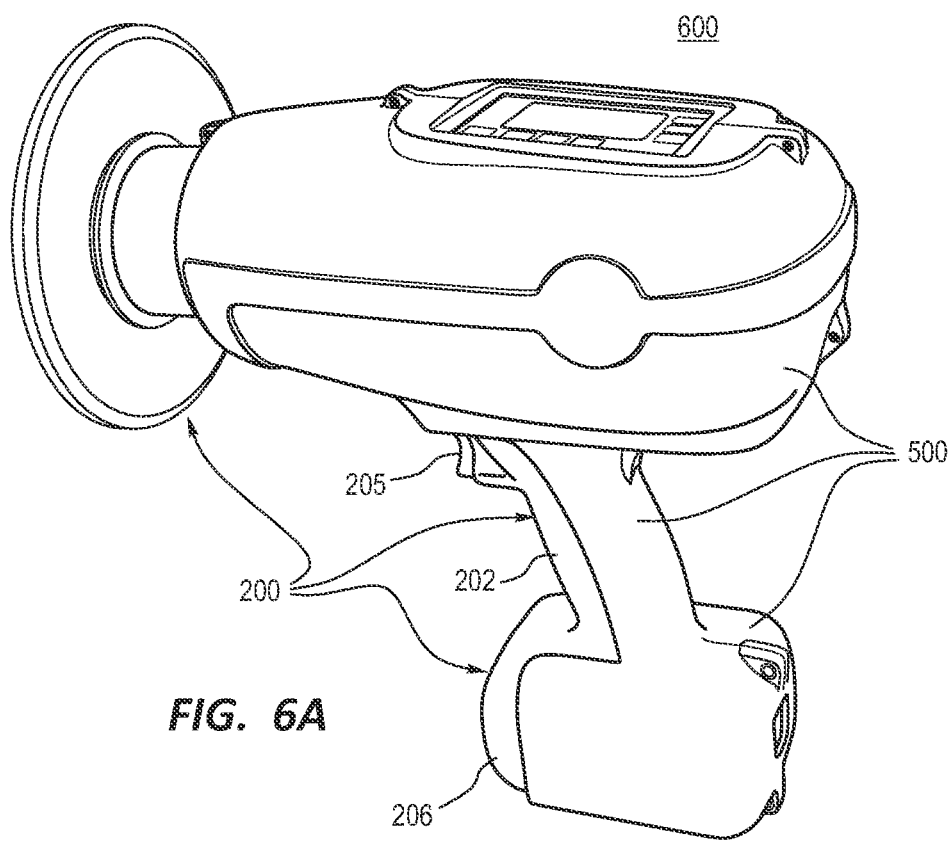
FIG. 6A is a left-back perspective view of a system that includes protective case that encases the handheld x-ray emitter device of FIG. 2, and is comparable to FIG. 5A.
Figure 6B:
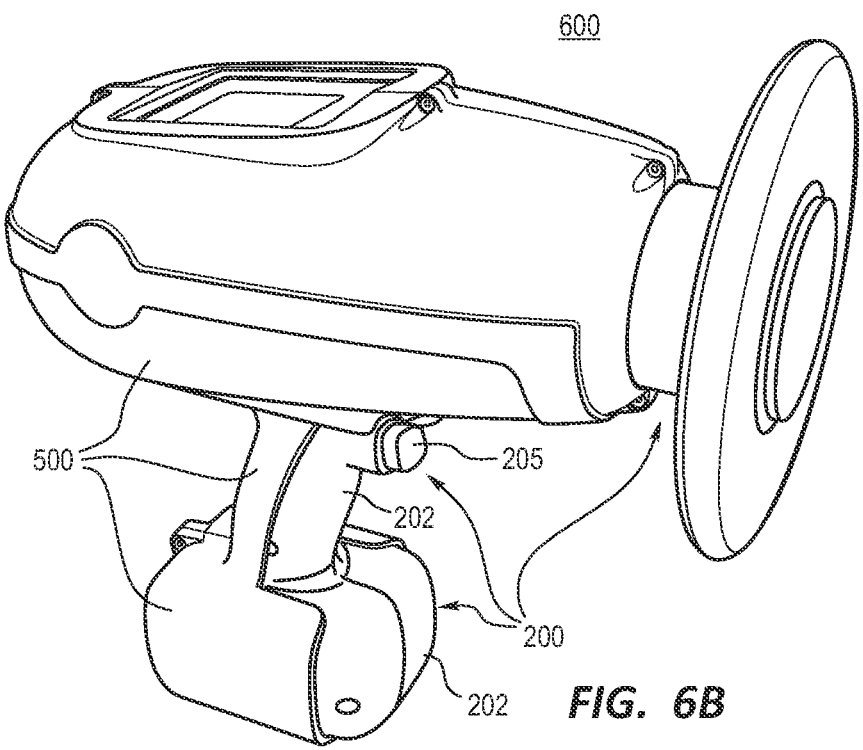
FIG. 6B is a right-front perspective view of the system of FIG. 6A that includes protective case that encases the handheld x-ray emitter device of FIG. 2, and is comparable to FIG. 5B.
Figure 6C:
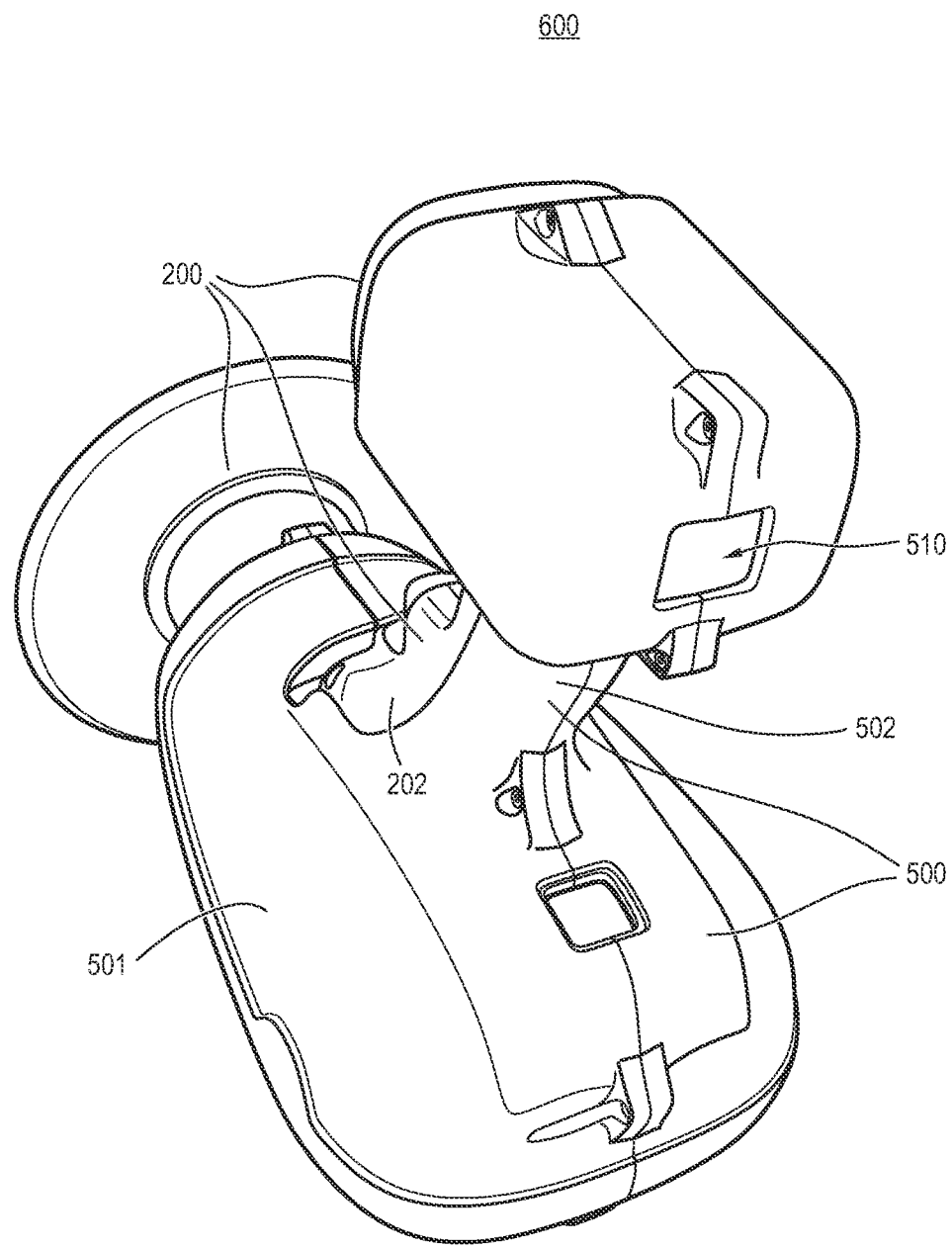
FIG. 6C is a bottom perspective view of the system of FIGS. 6A and 6B.

FIGS. 5A and 5B illustrate a protective case 500 in the closed state but not containing the handheld x-ray emitter device 200. FIG. 5A illustrates a left-back perspective view of the protective case 500, and FIG. 5B illustrates a right-front perspective view of the protective case 500. On the other hand, FIGS. 6A through 6C illustrates a system 600 that includes the protective case 500 when in the closed state and now containing the handheld x-ray emitter device 200. FIG. 6A illustrates a left-back perspective view of the system 600, and is comparable to FIG. 5A, except that now the protective case 500 encloses the handheld x-ray emitter device 200. FIG. 6B illustrates a right-front perspective view of the system 600, and is comparable to FIG. 6B. FIG. 6C is a lower perspective view of the system. Features of the protective case 500 and the system 600 will now be described with reference to FIGS. 5A, 5B and 6A through 6C.

The protective case 500 (the coupled combination of the left component 400A and right component 400B) includes a handle portion 502 that covers the trigger handle 202 of the handheld x-ray emitter device 200. The handle portion 502 still allows the trigger 205 of the handheld x-ray emitter device 200 to be activated while the handheld x-ray emitter device 200 is contained within the protective case 500. For instance, the left component 400A includes a recess 411A (see FIG. 4A) and the right component 400B includes an opposite recess 411B (see FIG. 4B).

When the left component 400A and the right component 400B are coupled, those two recess 411A and 411B form slide opening 505 through which the trigger 205 of the trigger handle 201 extends. This allows the trigger 205 to still be activated while the handheld x-ray emitter device 200 is contained within the protective case 500. Furthermore, the trigger handle 202 of the handheld x-ray emitter device 200 may be removed from the tube barrel 201 of the handheld x-ray emitter device 200 by sliding the handle portion 202 forward through the slide opening 505 with respect to the tube barrel 202 for charging of the battery. After charging, the trigger handle 202 may be reattached to the tube barrel by sliding the handle portion backwards through the slide opening 505 and with respect to the tube barrel 202.

The protective case 500 also includes a tube portion 501 that covers the tube barrel 201 of the handheld x-ray emitter device 200. The tube portion 501 is integrally connected to the handle portion 502. This connection helps to structurally reinforce the connection between the tube barrel 201 and the trigger handle 202 of the handheld x-ray emitter device 200 while the handheld x-ray emitter device is contained within the protective case 500. Also, when the handheld x-ray emitter device 200 is contained within the protective case 500, the protective case 500 contains the battery portion 206 of the handheld x-ray emitter device 200.

The protective case 500 also includes an emissions hole 503. When the handheld x-ray emitter device 200 is contained within the protective case 500, the front portion 203 of the handheld x-ray emitter device 200 is exposed at the emissions hole 503. The emissions hole 503 is formed from the mating of a space 412A in the left component 401A of the handheld x-ray emissions device with a corresponding space 412B in the right component 401B of the protective case 500.

The protective case 500 includes a display hole 504. When the handheld x-ray emitter device 200 is contained within the protective case 500, the display 204 of the handheld x-ray emitter device 200 is exposed through the display hole 504. The display hole 504 is formed from the mating of a rectangular notch 413A in the left component 401A of the handheld x-ray emissions device with a corresponding rectangular notch 413B in the right component 401B of the protective case 500.

As apparent from FIG. 6C, the handle portion 502 of the protective case includes a hole 510 that exposes a back the battery portion 206 of the handheld x-ray emitter device 200. This facilitates pushing the trigger handle 202 forward with respect to the tube barrel 201. This allows sufficient forward sliding force to be applied to slide the trigger handle 202 off of the tube barrel 201 in preparation for charging of the battery contained within the battery portion 206.

Figure 7:
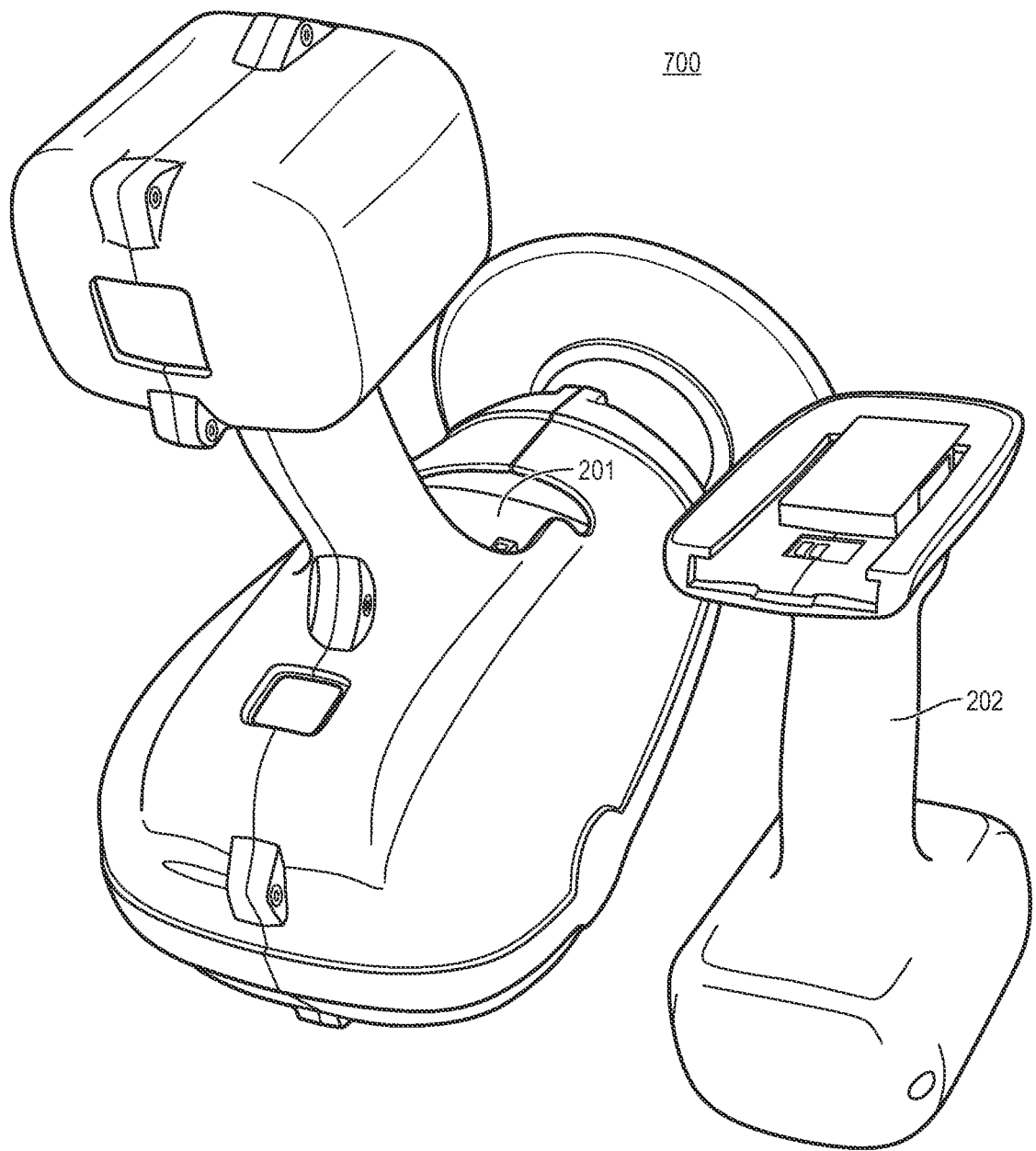
FIG. 7 illustrates a situation in which the trigger handle has been removed from the tube barrel, without having to dissemble the protective case.
Figure 8:
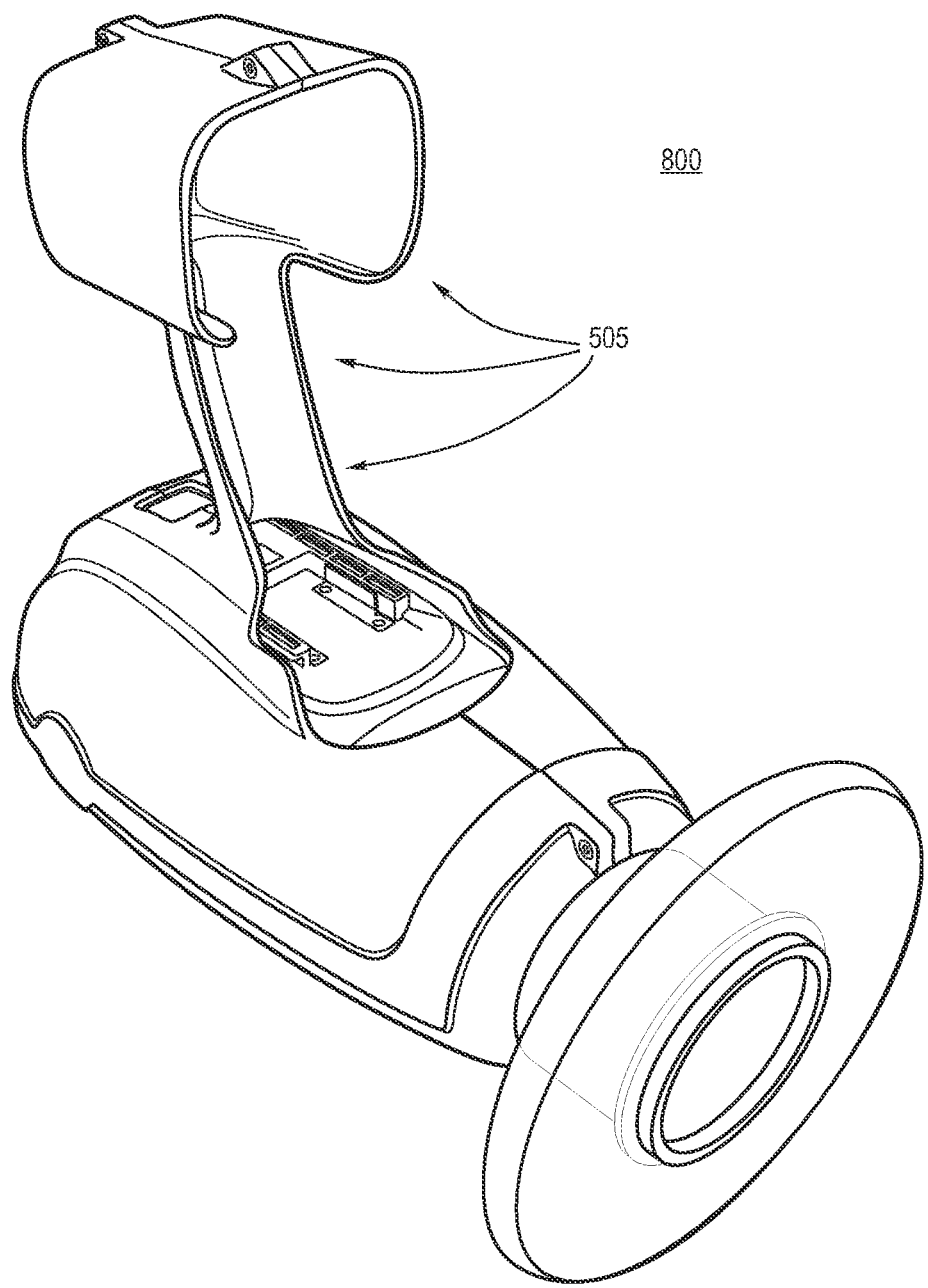
FIG. 8 illustrates a front view of the system in which the trigger handle has been removed by sliding forward through the slide opening.

FIG. 7 illustrates a situation in which the trigger handle 202 has been removed from the tube barrel 201, without having to dissemble the protective case. FIG. 8 illustrates a front view of the system 800 in which the trigger handle 202 has been removed by sliding forward through the slide opening 505.

Accordingly, the principles described herein provide for a protective case the structurally reinforces the handheld x-ray emitter device, particularly at the junction between the trigger handle and the tube barrel. In the illustrated embodiment of FIGS. 4A through 8, the protective case covers almost all of the handheld x-ray emitter device. However, the principles described herein are not limited to this kind of complete covering. A protective case that covers less of the handheld x-ray emitter device may still provide structural reinforcement to the junction between the tube barrel and trigger handle.

For example, the left component may be structured to cover only a part of the left portion of the handheld x-ray emitter device, and the right component may be structured to cover only a part of the right portion of the tube barrel. Nonetheless, the tube portion of the protective case still encircles at least some of the tube barrel. That is the tube portion of the protective case wraps around the circumference of the tube barrel, but only along a portion of the entire length of the tube barrel. However, the tube portion is still integrally connected to the handle portion of the coupled combination of the left component and the right component so as to structurally reinforce a connection between the tube barrel and the trigger handle of the handheld x-ray emitter device. However, the tube portion should still cover enough of the length of the tube barrel so that the tube portion is sufficiently structurally strong. In one embodiment, the tube portion of the protective case covers a majority of the tube barrel (e.g., by encircling the tube barrel along the majority of the length of the tube barrel).

As another example, the coupled combination of the left component and the right component has been described as forming a handle portion that covers most of the trigger handle except at the slide opening. However, in other embodiments, the handle portion may cover all of the handheld x-ray emitter device (except perhaps at a trigger hole that exposes the trigger). However, the handle portion may perhaps only cover a portion (e.g., a majority) of the trigger handle, such as a top region of the trigger handle. Nonetheless, the trigger portion is still integrally connected to the tube portion of the protective handle to structurally reinforce the junction between the underlying trigger handle and tube barrel of the handheld x-ray emitter device.

As a final note, the right component and the left component have been described as being non-destructively couplable and decouplable via one or more screw holes and associated screws. However, the principles described herein are not limited to that, but may include any mechanism for non-destructively coupling and decoupling the components of the protective case. As an example, this could include a finger control, latches, or the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A protective case for a handheld x-ray emitter device that has a tube barrel and a trigger handle connected to the tube barrel, the protective case comprising:

a left component structured to cover at least a part of a left portion of the handheld x-ray emitter device including at least a part of a left portion of the tube barrel of the handheld x-ray emitter device; and a right component structured to cover at least a part of a right portion of the handheld x-ray emitter device including at least a part of a right portion of the tube barrel of the handheld x-ray emitter device, the right component and the left component being further structured to be couplable to each other, such that 1) a coupled combination of the left component and the right component collectively includes a handle portion that is structured to cover a majority of the trigger handle of the handheld x-ray emitter device, while a trigger of the trigger handle is still activatable; and 2) the coupled combination of the left component and the right component includes a tube portion that encircles at least some of the tube barrel and that is integrally connected to the handle portion of the coupled combination of the left component and the right component so as to structurally reinforce a connection between the tube barrel and the trigger handle of the handheld x-ray emitter device.

2. The protective case in accordance with claim 1, the right component and the left component being further structured to be removably couplable to each other, such that the right component and the left component are non-destructively decouplable.

3. The protective case in accordance with claim 1, the right component and the left component being further structured such that the coupled combination of the right component and left component includes a front portion of the tube barrel that is exposed at an emissions hole formed in the coupled combination of the right component and left component.

4. The protective case in accordance with claim 1, the right component and the left component being further structured such that the handle portion of the coupled combination includes a slide opening through which the trigger handle can be slid to remove the trigger handle from the tube barrel without decoupling the right component from the left component of the protective case.

5. The protective case in accordance with claim 4, the coupled combination of the right component and left component being further structured such that the trigger of the trigger handle is exposed at the slide opening formed in the coupled combination of the right component and left component.

6. The protective case in accordance with claim 1, the right component and the left component being further structured such that a display on the tube barrel is exposed through a display hole formed in the coupled combination of the right component and left component.

7. The protective case in accordance with claim 1, each of the right component and left component composed of plastic.

8. The protective case in accordance with claim 1, each of the right component and left component composed of a non-gelatinous solid material.

9. The protective case in accordance with claim 1, the right component and the left component being structured such that the coupled combination of the right component and the left component is structured to cover most of the tube barrel of the handheld x-ray emitter device.

10. The protective case in accordance with claim 1, the right component and the left component being structured such that the coupled combination of the right component and the left component is structured to collectively contain a battery portion of the handheld x-ray emitter device that is connected to an opposite end of the trigger handle than of the end of the trigger handle to which the tube barrel is connected.

11. A system comprising:
a handheld x-ray emitter device that comprises a tube barrel and a trigger handle connected to the tube barrel; and
a protective case protecting the handheld x-ray emitter device, the protective case comprising:
a left component that covers at least a part of a left portion of the handheld x-ray emitter device including at least a part of a left portion of the tube portion of the handheld x-ray emitter device; and
a right component that covers at least a part of a right portion of the handheld x-ray emitter device including at least a part of a right portion of the tube barrel of the handheld x-ray emitter device, the right component and the left component being structured such that the coupled combination of the right component and the left component collectively includes a handle portion that cover a majority of the trigger handle of the handheld x-ray emitter device, but a trigger of the trigger handle is still activatable; and the coupled combination of the right component and the left component includes a tube portion that encircles at least some of the tube barrel and is integrally connected to the handle portion of the coupled combination of the right component and the left component so as to structurally reinforce a connection between the tube barrel and the trigger handle of the handheld x-ray emitter device.

12. The system in accordance with claim 11, the right component and the left component being further structured to be removably couplable and non-destructively decouplable to each other.

13. The system in accordance with claim 11, wherein a front portion of the tube barrel is exposed at an emissions hole formed in the coupled combination of the right component and left component.

14. The system in accordance with claim 11, the right component and the left component being further structured such that the handle portion of the coupled combination includes a slide opening through which the trigger handle can be slid to remove the trigger handle from the tube barrel without decoupling the right component from the left component of the protective case.

15. The system in accordance with claim 14, wherein the trigger of the trigger handle is exposed at the slide opening formed in the coupled combination of the right component and left component.

16. The system in accordance with claim 11, wherein the trigger of the trigger handle is exposed at a trigger hole formed in the coupled combination of the right component and left component.

17. The system in accordance with claim 11, wherein a display on the tube barrel is exposed through a display hole formed in the coupled combination of the right component and left component.

18. The system in accordance with claim 11, wherein each of the right component and the left component are composed of plastic.

19. The system in accordance with claim 11, wherein each of the right component and left component are composed of a non-gelatinous solid material.

20. The system in accordance with claim 11, wherein
the coupled combination of the right component and the left component collectively covers most of the tube barrel of the handheld x-ray emitter device; and
the coupled combination of the right component and the left component collectively contains a battery portion of the handheld x-ray emitter device that is connected to an opposite end of the trigger handle than of the end of the trigger handle to which the tube barrel is connected.

\* \* \* \* \*